United States Patent [19]
Kaminishi et al.

[11] Patent Number: 5,793,073
[45] Date of Patent: Aug. 11, 1998

[54] SEMICONDUCTOR THIN FILM SENSOR DEVICE WITH (110) PLANE

[75] Inventors: Morimasa Kaminishi, Shiroishi; Takayuki Yamaguchi, Minoo; Yukito Satoh, Sendai, all of Japan

[73] Assignee: Ricoh Co., Ltd., Tokyo, Japan

[21] Appl. No.: 613,447

[22] Filed: Mar. 1, 1996

[30]   Foreign Application Priority Data

Mar. 1, 1995 [JP] Japan .................... 7-041485

[51] Int. Cl.$^6$ ............................................ H01L 29/82
[52] U.S. Cl. ................... 257/254; 257/417; 257/418; 257/619; 257/627; 73/514.21; 73/514.22; 73/514.36; 73/514.37; 73/754
[58] Field of Search ..................... 257/627, 419, 257/418, 417, 253, 254, 252, 619, 628; 73/754, 514.21, 514.22, 514.36, 514.37

[56]              References Cited

U.S. PATENT DOCUMENTS

| | | | |
|---|---|---|---|
| 4,478,077 | 10/1984 | Bohrer et al. .................. 257/622 X |
| 4,682,503 | 7/1987 | Higashi et al. .................. 257/627 X |
| 4,975,390 | 12/1990 | Fujii et al. .................. 437/228 |
| 5,155,061 | 10/1992 | O'Connor et al. .................. 437/86 |
| 5,594,171 | 1/1997 | Ishida et al. .................. 73/514.32 |

FOREIGN PATENT DOCUMENTS

1-239882  9/1989  Japan ........................ 257/417

*Primary Examiner*—William Mintel
*Attorney, Agent, or Firm*—Oblon, Spivak, McClelland, Maier & Neustadt, P.C.

[57]              ABSTRACT

A semiconductor thin film sensor device including a semiconductor body formed of silicon having a (110) plane; a depression formed by an anisotropic etch applied to a first surface of the semiconductor body, wherein the first surface is substantially parallel to the (110) plane; and a thin film insulation member having a predetermined configuration suspended over the depression, and having substantially opposing ends connected to the first surface of the semiconductor body so that the thin film insulation member is bridged across the depression. Preferably, the depth of the depression is over 200 μm. In one embodiment, the predetermined configuration of the thin film insulation member is oriented substantially parallel to a <100> direction of the semiconductor body.

10 Claims, 11 Drawing Sheets

*FIG. 1*

BACKGROUND ART

*FIG. 2*

BACKGROUND ART

SEMICONDUCTOR THIN FILM SENSOR DEVICE WITH (110) PLANE

BACKGROUND OF THE INVENTION

1. Field of the Invention

The present invention relates to integrated semiconductor device technology in the field of sensors, and more particularly to a thin film sensor device suspended over a depression of a semiconductor body for measuring various physical properties of gas, for example humidity, an appearance of combustible gas or a flowing velocity, or flow volume.

2. Discussion of the Background

Various sorts of sensors for measuring various physical properties of gas are known, including one in which a thin film sensor is suspended over a depression of a semiconductor body, such as has been used for a humidity sensor, a combustible gas sensor or a gas flow sensor etc.

Figure 1:
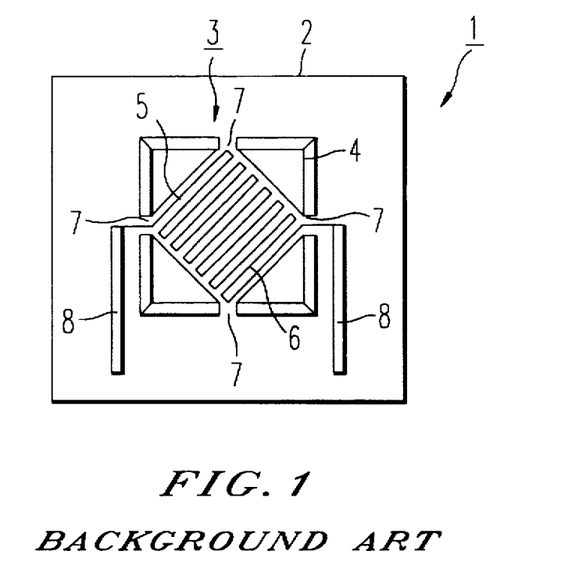
FIG. 1 is a plan view of an example of conventional humidity sensor device.

FIG. 1 shows an example of a conventional humidity sensor 1.

A thin film sensor 3 is suspended over a square depression 4 of a semiconductor body 2 so that a square thin film body 5 of the sensor 3 is bridged across the depression 4 at four bridge portions 7. A heat sensitive part 6 is formed on the thin film body 5, and electric terminals 8 are formed on a surface of the semiconductor body 2 and connected to the heat sensitive part 6 at a surface of two of the bridge portions 7. The terminals 8 are supplied with a uniform electric power, and the heat sensitive part 6 is heated at a uniform temperature. However, the resistance of the heat sensitive part 6 varies due to the temperature variation of the part 6 accompanying a humidity variation, and thereby the humidity can be measured by measuring the resistance value of the heat sensitive part 6.

Figure 2:
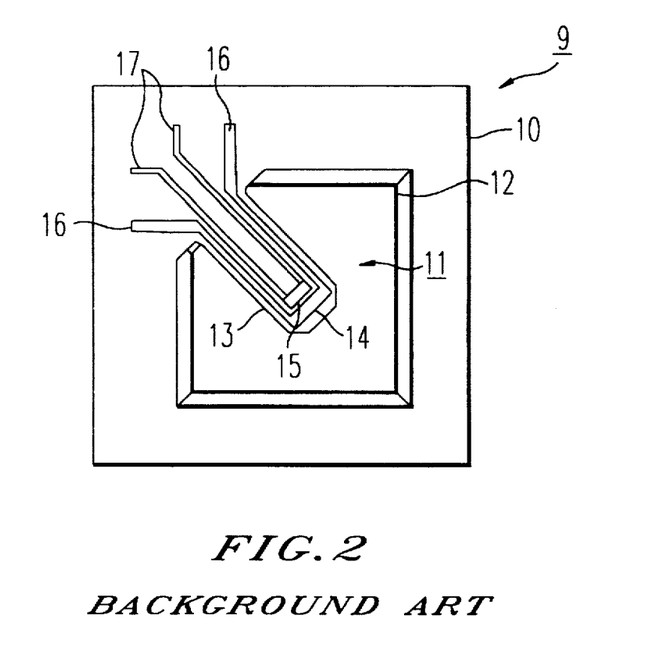
FIG. 2 is a plan view of an example of conventional combustible gas sensor device.

FIG. 2 shows an example of a conventional combustible gas sensor 9.

A thin film sensor 11 is suspended over a square depression 12 of a semiconductor body 10 so that a thin film body 13 of the sensor 11 is bridged across the depression 12 at a corner of the depression 12. A heater 14 and a sensing portion 15 are formed on the thin film body 13. An electric terminal 16 is formed to connect to the heater 14, and an electric terminal 17 is formed to connect to the sensing portion 15. The sensing portion 15 is made of a tin oxide, which when heated by the heater 14 tends to adsorb a particular kind of gas (e.g. propane). As a result, a resistance value of the sensing portion 15 varies due to adsorbing the particular gas, and thereby an appearance of the particular gas can be determined.

Figure 3:
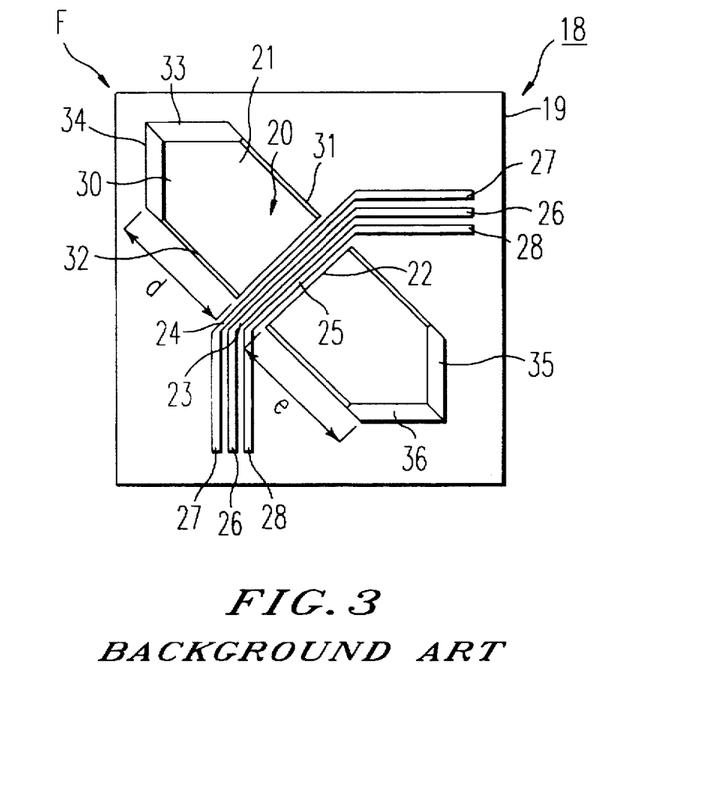
FIG. 3 is a plan view of an example of conventional gas flow sensor device.

FIG. 3 shows one example of a conventional gas flow sensor 18.

A thin film sensor 20 is suspended over a depression 21 of a semiconductor body 19 oriented substantially parallel to a flow direction F of a gas, so that a bridge-like thin film body 22 of the sensor 20 is bridged across the depression 21. A first sensing portion 24, a second sensing portion 25 and a heater 23 are formed on the thin film body 22. An electric terminal 26 is formed to connect to the heater 23, an electric terminal 27 is formed to connect to the sensing portion 24, and an electric terminal 28 is formed to connect to the sensing portion 25.

In case the gas does not flow in the flow direction F, the first sensing portion 24 is heated the same as the second portion 25 by the heater 23. However, in case the gas flows in the direction F, the second sensing portion 25 is heated more than the first sensing portion 24 by the warm gas heated by the heater 23. As resistance values of the sensing portions 24, 25 vary due to the temperature variation, a flowing velocity or a flowing volume of the gas can be measured by the resistance value difference between the first sensing portion 24 and the second sensing portion 25.

In the foregoing sensor, a heat-sensitive part of the sensor is formed on a bridge-like thin film body so that the heat capacitance of the heat-sensitive part can be decreased, the heat loss on the substrate and the substrate supporter can be reduced, and furthermore the supplied electric power required for heating can be also reduced.

A depression of a semiconductor body as above described is typically formed by an anisotropic etch applied to a first surface of the body made of silicon. Silicon has (100), (110) and (111) crystal planes, and the speed of the anisotropic etch perpendicular to these crystal planes is as follows:

(100)>(110)>>(111).

A structure of depression and a undercutting of the thin film body can be made by the difference of etching speed.

Figure 4A:
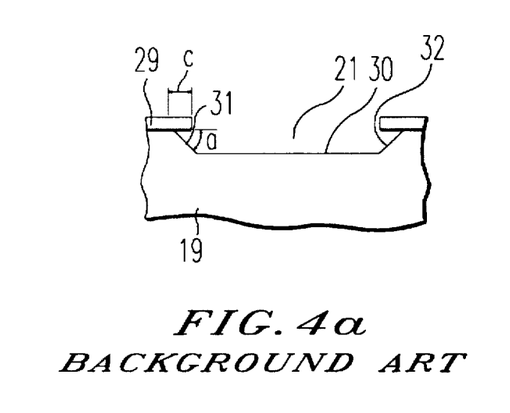
FIGS. 4(a) and 4(b) are fragmentary sectional views of the conventional sensor device as shown FIG. 3.
Figure 4B:
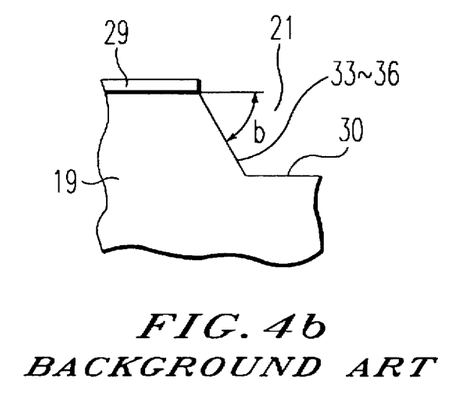

The way of making the structure of a depression and the undercutting of the thin film body of the forgoing sensors, is next explained referring to FIGS. 3, 4(a) and 4(b), for example.

In the foregoing background sensors, a thin film insulation member 29 is formed on a silicon having (100) plane. Using a suitable photo mask, a photoresist, and a suitable etchant, a predetermined opening that is formed in the thin film body 22 is made on the thin film insulation member 29, i.e., a surface of silicon is bared in the opening. Finally, using KOH plus isopropyl alcohol as a suitable etchant, an anisotropic etchant is used to form the depression and undercutting of the thin film body 22. As a result, the structure of the depression 21 and the bridge-like thin film body 22 is made.

Figure 5:
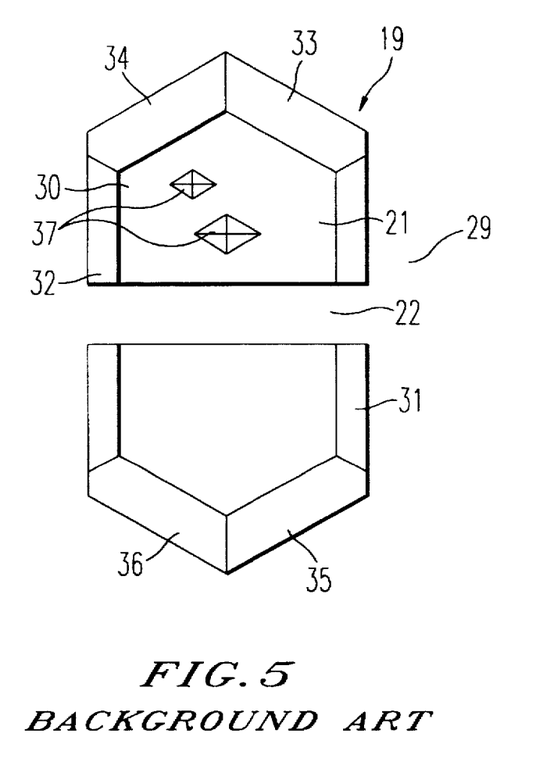
FIG. 5 is a plan view showing a convex portion made on a bottom of a depression of the conventional sensor device as shown FIG. 3.

The depression 21 has a bottom 30 and six wells 31–36 as shown in FIG. 3–FIG. 5.

Four walls 33–36 of the six are in the (111) plane of the silicon, wherein the anisotropic etch is hardly proceeded. As shown FIG. 4 (b), these walls 33–36 do not undercut the thin film insulation member 29.

Other walls 31, 32 are not in crystal planes in which the anisotropic etch proceeds with greater ease; these walls 31, 32 are etched to undercut the thin film insulation member 29 as shown FIG. 4(a).

In this connection, an angle "a" in FIG. 4(a) is 45° and an angle "b" in FIG. 4(b) is 55.7°, as determined by inventor experimentation.

In the forgoing background sensor, a lattice defect of the silicon probably makes one or more convex portions 37 formed like a quadrangular pyramid on the bottom 30 of the depression 21, as shown in FIG. 5. The convex portions substantially adversely affect physical and thermal isolation, and promote turbulence.

As the thin film insulation member 29 is undercut by the sloping walls 31 and 32 shown in FIG. 4(a), the thin film insulation member 29, especially the bridge-like thin film body 22, is fragile at the point of connection to walls 31 and 32. The undercut length "c" is the same of the depth of the depression 21 because the angle "a" is 45°. The length "c" is made large in proportion to the required depth.

SUMMARY OF THE INVENTION

Accordingly, one object of this invention is to provide a novel thin film sensor device which avoids the drawbacks of the conventional sensor devices.

3

In accordance with the present invention, this object is attained by providing a novel thin film sensor device which includes a semiconductor body comprising silicon having a (110) plane, a depression formed by an anisotropic etch applied to a first surface of the semiconductor body, wherein the first surface is substantially parallel to the (110) plane, and a thin film insulation member having a predetermined configuration suspended over the depression, and having substantially opposing ends connected to the first surface of the semiconductor body so that the thin film insulation member is bridged across the depression.

Such a thin film sensor device may also find application in the predetermined configuration with the thin film insulation member oriented substantially parallel to the <110> direction of the semiconductor body or the <111> direction of the semiconductor body.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawing, wherein:

FIG. 15(a), FIG. 15(b) and FIG. 15(c) are partial sectional views of a modification of the foregoing thin film sensor shown in FIG. 14 taken along the line I—I', in which FIG. 15(a) shows the portion of the sensor to the right of line A—A', FIG. 15(b) shows the portion of the sensor to the left of the line B—B', and FIG. 15(c) shows the portion of the sensor between the lines A—A' and B—B';

DETAILED DESCRIPTION OF THE PREFERRED EMBODIMENTS

Figure 6:
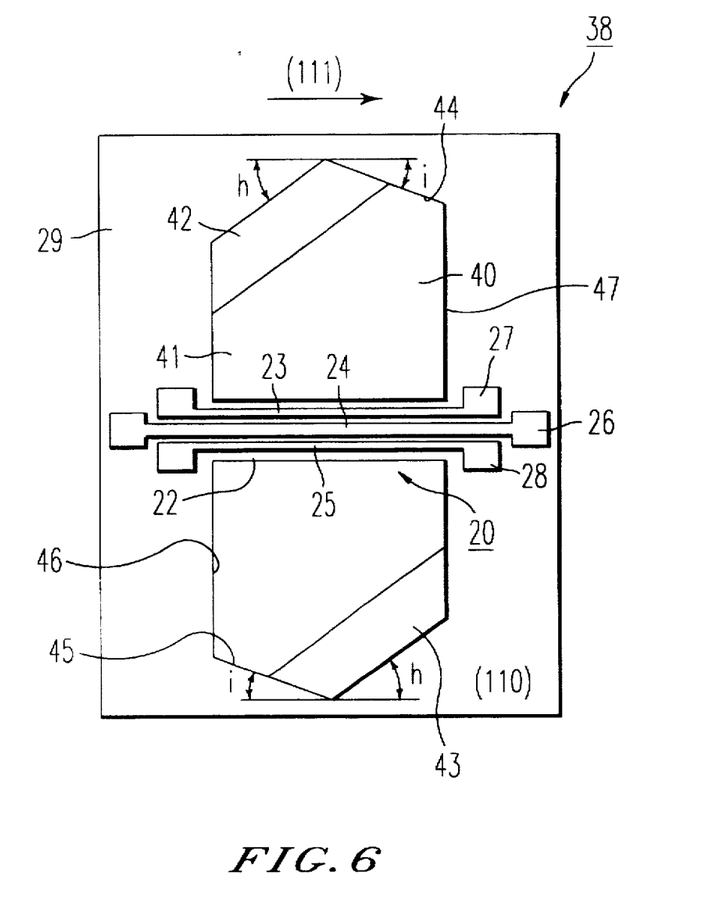
FIG. 6 is a plant view of an embodiment of the present invention in which a thin film sensor is suspended over a depression of a silicon body having a (110) plane, and is oriented parallel to a <111> direction.
Figures 7A, 7B:
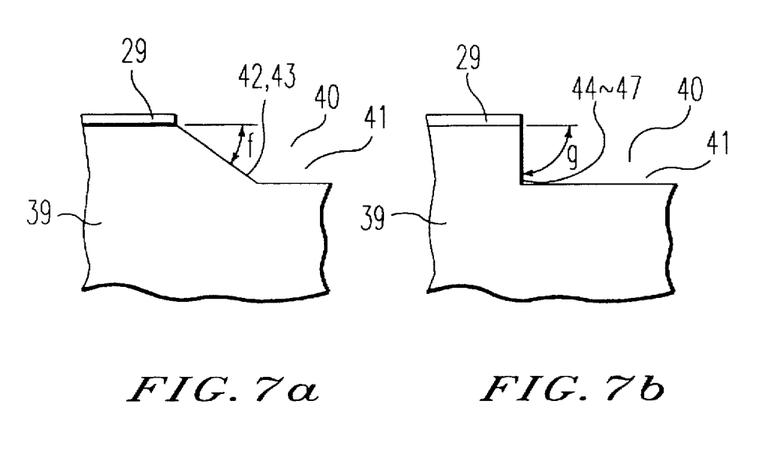
FIGS. 7(a) and 7(b) are fragmentary sectional views of the sensor device as shown FIG. 6.

Referring now to the drawings, wherein like reference numerals designate identical or corresponding parts throughout the several views, and more particularly to FIG. 6, FIG. 7(a) and 7(b) thereof, there is shown a thin film sensor device 38 according to the present invention working as gas flow sensor, having a depression 40 on a silicon body 39 having a (110) plane and a thin film sensor 20 suspended over the depression 40 and being oriented parallel to a <111> direction.

As shown in FIG. 6, FIG. 7(a) and FIG. 7(b), the depression has a bottom 41, two sloping walls 42 and 43, and four vertical walls 44–47. The depth of the depression 40 is 200 μm or more. The length of the walls 47 and 46 is 0.3 mm or more. As shown in FIGS. 7(a) and 7(b), the angle "f" is 35.26° and the angle "g" is 90°. As shown in FIG. 6, the angle "h" is 35.26°, and the angle "i" is 19.47°.

In fabrication of the above-described device, for example, a layer of a thin film insulation member 29 having a thickness 1.0 μm and made of $SiO_2$ is formed on a surface of a (110) plane of a silicon wafer by sputtering. Then a layer of a thin film metal member having a thickness 0.5 μm and made of Pt is formed on the thin film insulation member 29 by sputtering. Using a suitable photo mask, a photoresist, and a suitable etchant, a heater 23 and a first and a second sensing portion 24, 25 is formed from the thin film metal member. Using a suitable photo mask, a photoresist, and a suitable anisotropic etchant, the opening of depression 40 is formed from the thin film insulation member 29. Finally, a suitable anisotropic etchant, such as 5.0% KOH plus isopropyl alcohol, is used to form the depression and undercutting of the thin film body 22, with the result being formation of the opening structure of depression 40 and the bridge-like thin film body 22.

As the thin film insulation member, $Si_3N_4$ or $Ta_2O_5$ may be used instead of the foregoing $SiO_2$, and a CVD (Chemical Vapor Deposition) process may be used instead of the foregoing sputtering. As the thin film metal member, Ni or Cr may be used instead of the foregoing Pt.

In the foregoing embodiment, the anisotropic etching at the bottom 41 proceeds quickly because the bottom 41 of the depression 40 is the (110) plane of the silicon wafer 39, the anisotropic etching at the walls 42 and 43 having the angle "h"=35.26° against the <111> direction proceeds to the angle "f"=35.26°, the anisotropic etching at the walls 44–47 having the angle "i"=19.47° against the <111> direction proceeds to an angle "g"=90° because the walls 44–47 are in the (111) plane. The anisotropic etching at both sides of the thin film body 22 proceeds to undercut the body 22 because the both sides of the body 22 are not in crystal planes.

Figure 8:
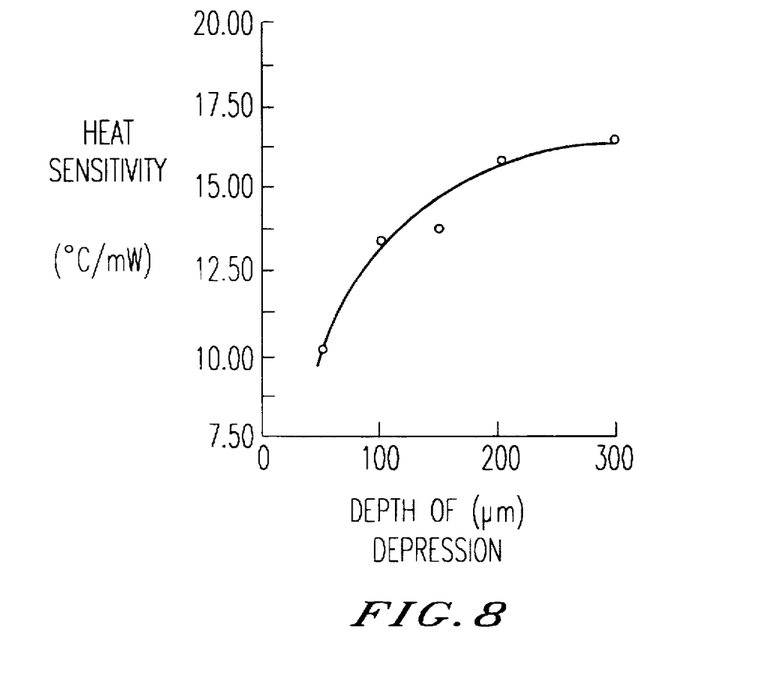
FIG. 8 is a graph showing a relation between a heat sensitivity of a thin film body and a depth of a depression in an embodiment of the present invention.

According to experiments by the inventor, the depth of the depression should be 200 μm or more as shown FIG. 8.

In case of an existing lattice defect in the silicon, in the present invention, a (111) plane appears under the lattice defect. The anisotropic etchant proceeds slowly at the (111) plane, with the result that the bottom of the depression is made planar without the convex portion experienced in the prior art. According to the experiments of the inventor, none of ten samples had the convex portion.

Figure 9:
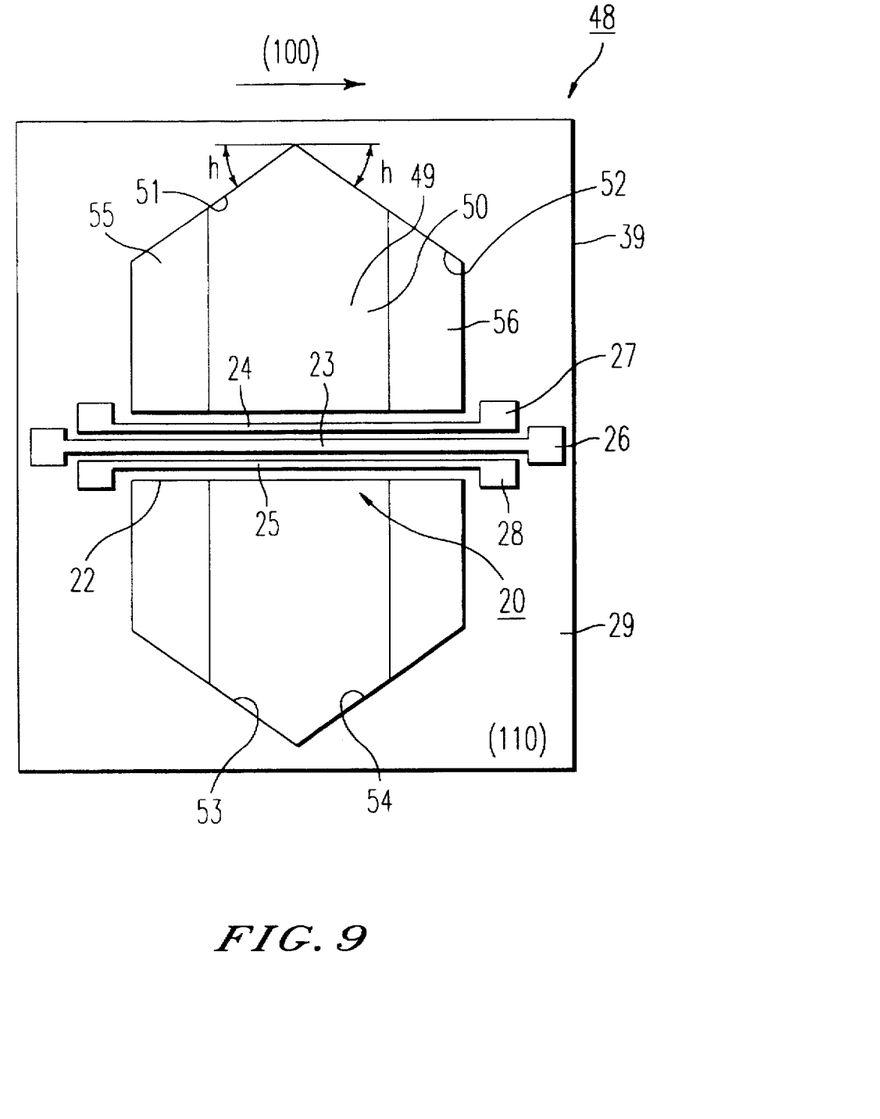
FIG. 9 is a plan view of another embodiment of the present invention in which a thin film sensor is suspended over a depression of a silicon body having a (110) plane, and is oriented parallel to a <100> direction.
Figures 10A, 10B:
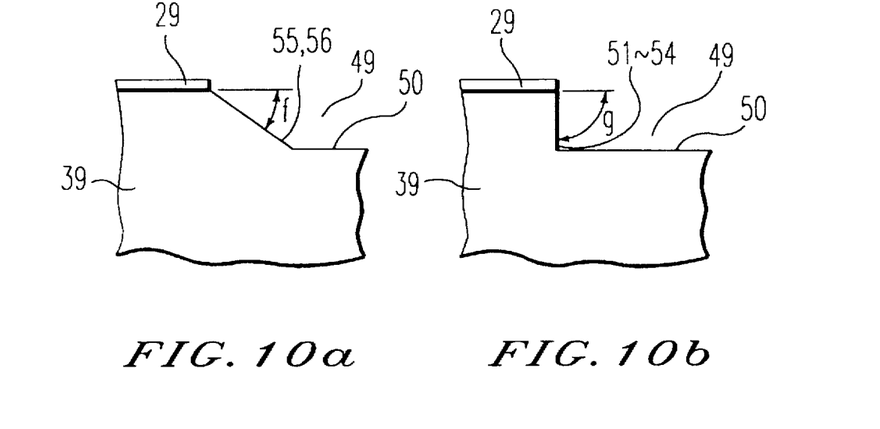
FIGS. 10(a) and 10(b) are fragmentary sectional views of the sensor device as shown FIG. 9.

FIG. 9, FIG. 10(a) and FIG. 10(b) show another embodiment of the present invention, which is a thin film sensor device 48 working as a gas flow sensor, having a depression 49 on a silicon body 39 having a (110) plane and a thin film sensor 20 being suspended over the depression 49 and oriented parallel to a <100> direction. As shown, the depression has a bottom 50, two sloping walls 55 and 56, and four vertical walls 51–54. The depth of the depression 49 is 200 μm or more. The angle "f" is 35.26°, the angle "g" is 90° and the angle "h" is 35.26°.

In this embodiment, the anisotropic etching at the bottom 50 proceeds quickly because the bottom 50 of the depression 49 is the (110) plane of the silicon wafer 39, the anisotropic etching at the walls 55 and 56 having the angle 90° against the <111> direction proceeds to an angle "f"=35.26°, the anisotropic etching at the walls 51–54 having the angle "h"=35.26° against the <111> direction proceeds to an angle "g"=90° because the walls 51–54 are in the (111) plane.

Figure 11:
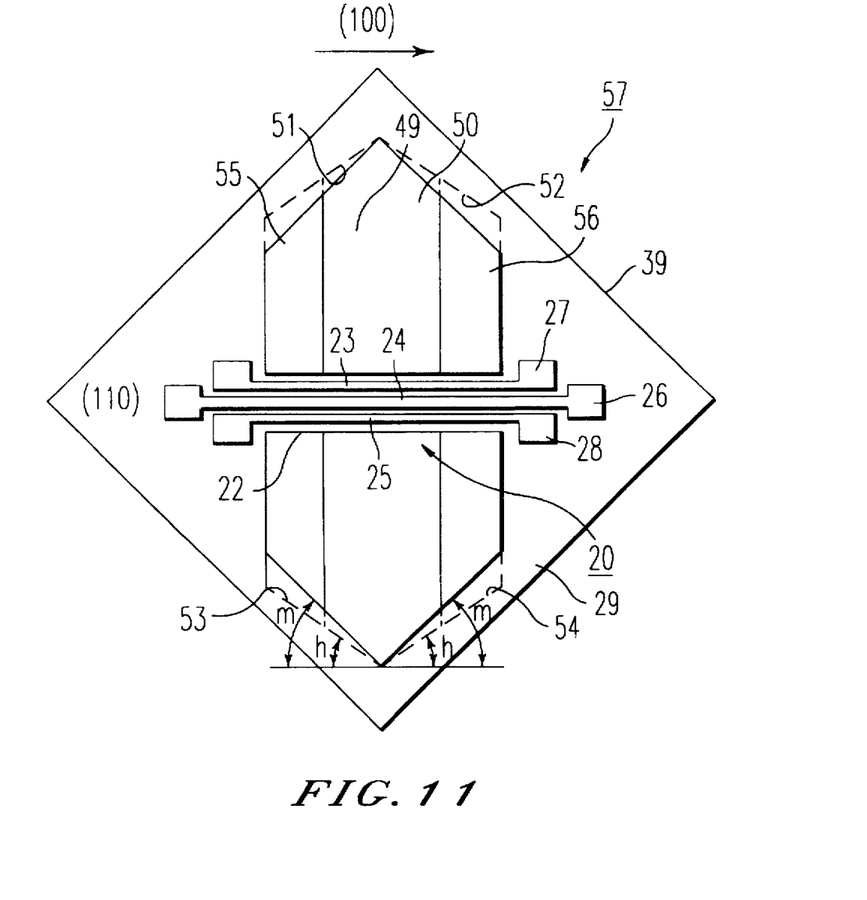
FIG. 11 is a plan view of a modification of the embodiment as shown FIG. 9 in which an angle of four slopes against the <100> direction is 45°.

Referring to FIG. 11, there is shown a modification of the second embodiment as shown FIG. 9. The thin film sensor device 57 shown in FIG. 11 is similar to that described above in FIG. 9 with the exception that the angle of walls 51–54 against the <100> direction is "m"=45°.

Figure 12:
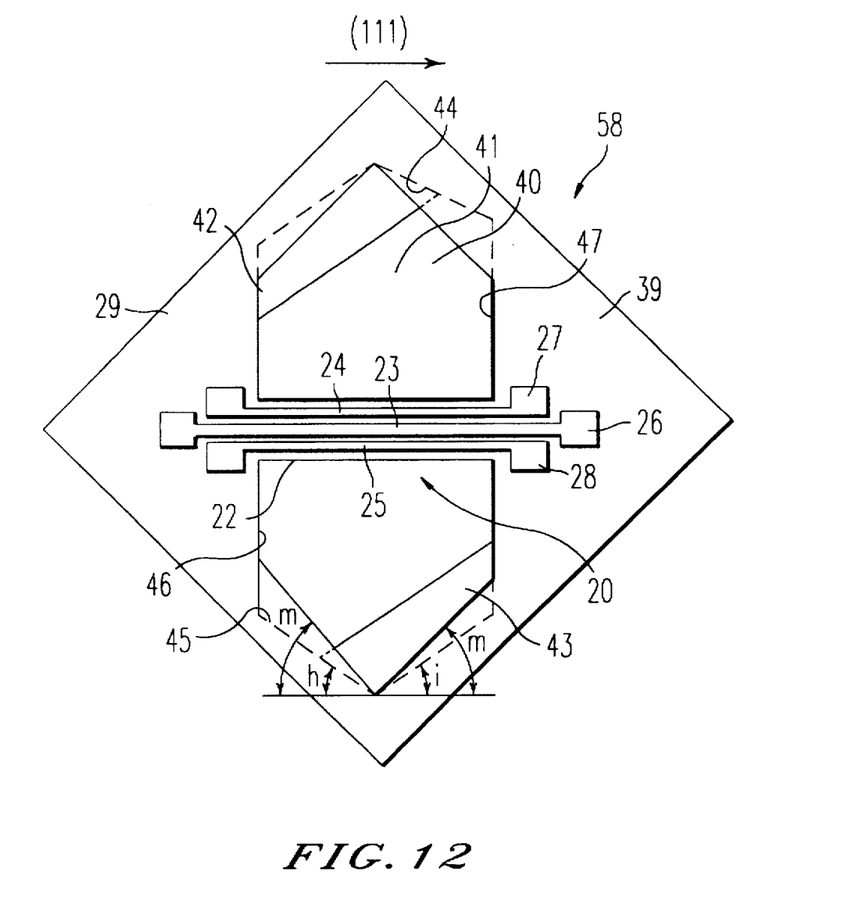
FIG. 12 is a plan view of a modification of the embodiment as shown FIG. 6 in which an angle of four slopes against the <100> direction is 45°.

Referring to FIG. 12, there is shown a modification of the second embodiment as shown FIG. 6. The thin film sensor device 58 shown in FIG. 12 is similar to that described above in FIG. 6 with the exception that the angle of walls 42–45 against the <100> direction is "m"=45°.

Figure 13:
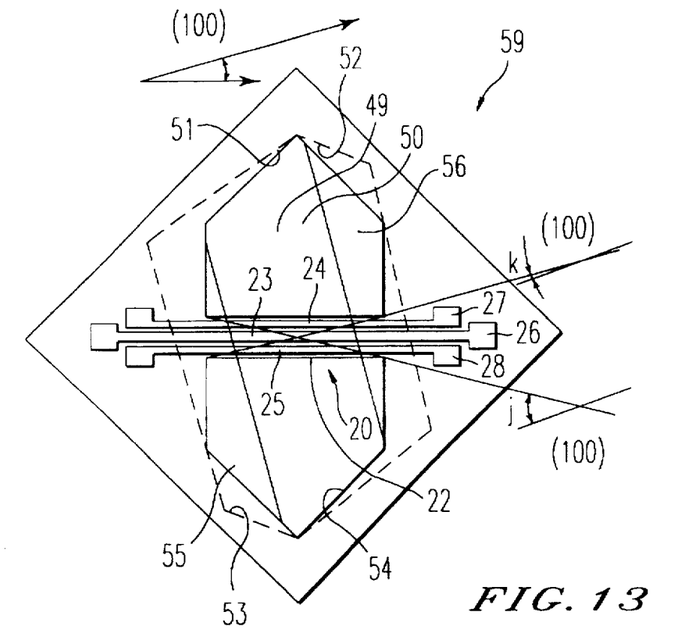
FIG. 13 is a plan view of a modification of the embodiment as shown FIG. 9 in which a thin film sensor is oriented at an angle to the <100> direction.

Referring to FIG. 13, there is shown a modification of the second embodiment as shown FIG. 9. The thin film sensor device 59 shown in FIG. 13 is similar to that described above in FIG. 9 with the exception that the thin film sensor 20 suspended over the depression 49 is oriented at an angle to the <100> direction. In this embodiment, only one of the angles "j" and "k" has to be under 35.26°.

Figure 14:
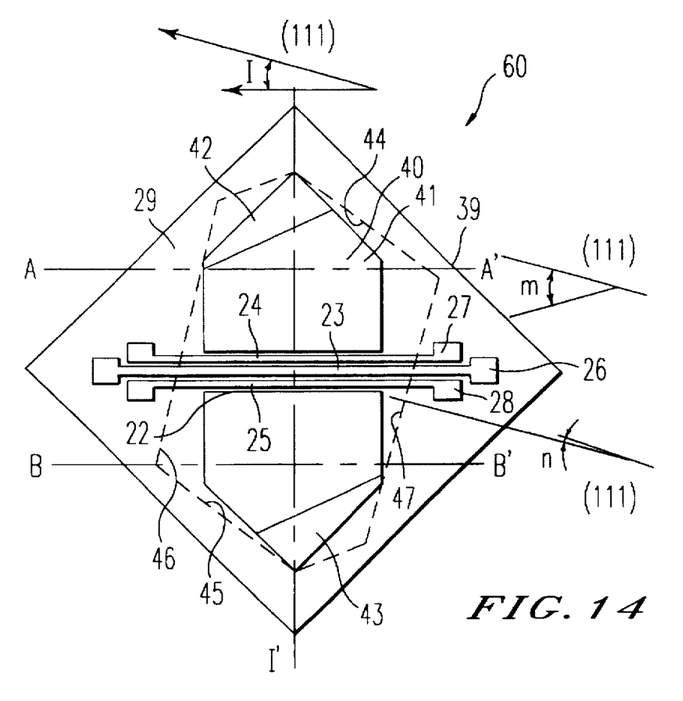
FIG. 14 is a plan view of a modification of the embodiment as shown FIG. 6 in which a thin film sensor is oriented at an angle to the <111> direction.

Referring to FIG. 14, there is shown a modification of the second embodiment as shown FIG. 6. The thin film sensor device 60 shown in FIG. 14 is similar to that described above in FIG. 6 with the exception that the thin film sensor 20 suspended over the depression 49 is oriented at an angle to the <111> direction. In this embodiment, the only one of angles "n" and "m" has to be under 19.47°. The other of these angles "n" and "m" may be 35.26°.

Figure 15A:
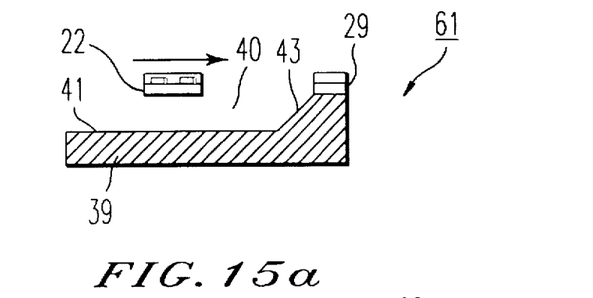
Figure 15B:
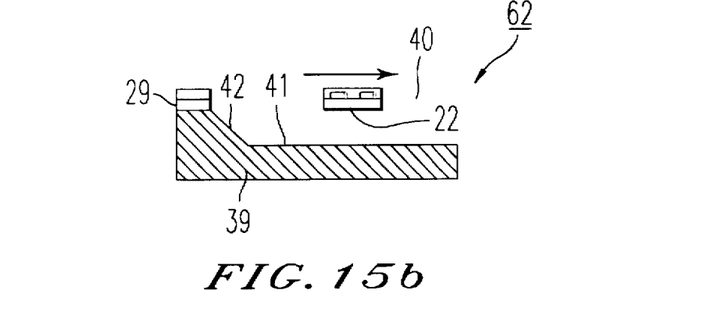
Figure 15C:
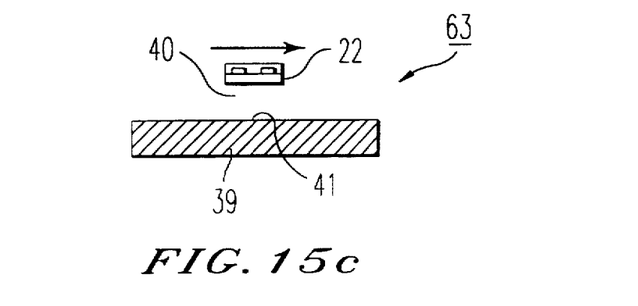

Referring to FIGS. 15(a), 15(b) and 15(c), a modification of the forgoing embodiments is there shown by means of sectional views taken along the line I—I' of the sensor shown in FIG. 14. The thin film sensor portion 61 shown in FIG. 15(a) is the front part of the sensor, i.e., the portion to the right of the line A—A' shown in FIG. 14 when looking to the right in FIG. 14. The sensor portion 62 shown in FIG. 15(b) is the rear part of the sensor, i.e., the portion to the left of the line B—B' shown in FIG. 14 when looking to the right in FIG. 14. The sensor portion 63 shown in FIG. 15(c) is a central part of the sensor, i.e., the portion between the lines A—A' and B—B' shown in FIG. 14.

Figure 16:
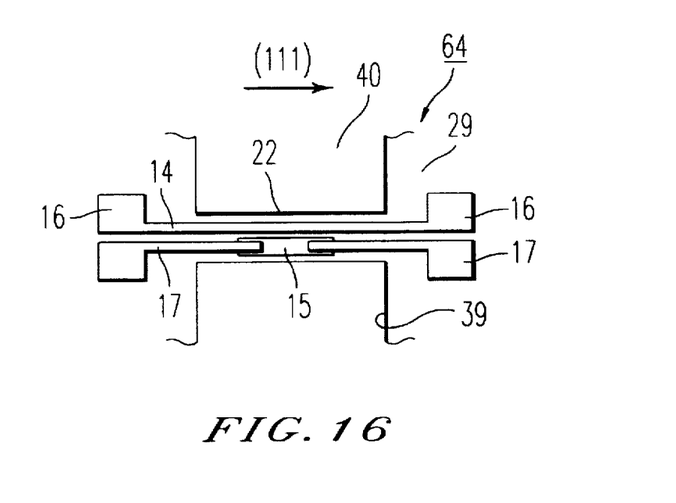
FIG. 16 and FIG. 17 are plan views of a modification of the embodiments as a combustible gas sensor.
Figure 17:
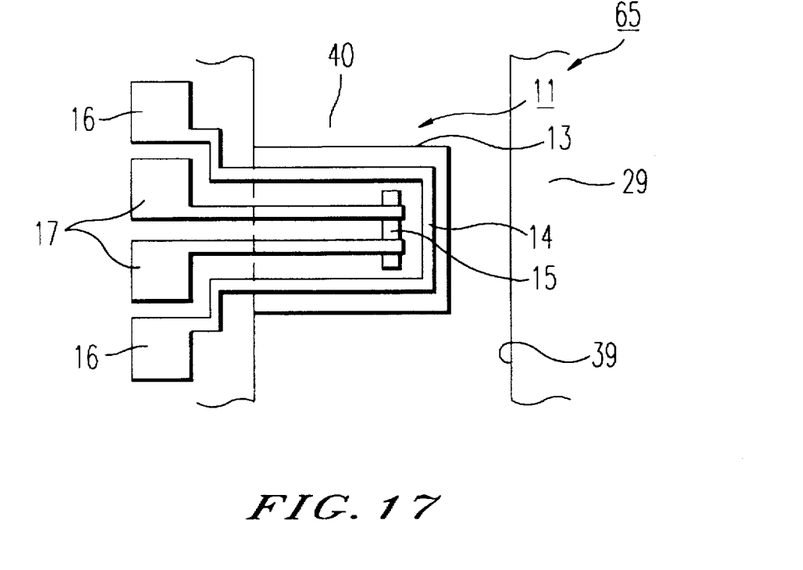
Figure 18:
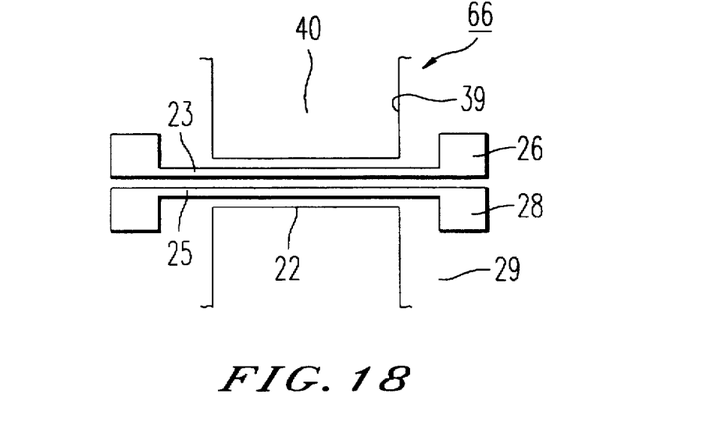
FIG. 18 is plan view of a modification of the embodiment of a gas flow sensor in which a thin film sensor has only one sensing element as a sensing portion.

Referring to FIG. 16 and FIG. 17, there is shown a modification of the forgoing embodiments for use as a combustible gas sensor 64, 65. In this connection, the forgoing embodiments may also be modified to implement a humidity sensor or other types of sensors. As shown in FIG. 18, a sensor 66 with only a single sensing element, i.e., without the sensing portion 24 of the forgoing embodiment, can be functional as a gas flow sensor.

Obviously, numerous additional modifications and variations of the present invention are possible in light of the above teachings. It is therefore to be understood that within the scope of the appended claims, the present invention may be practiced otherwise than as specifically described herein.

What is claimed as new and is desired to be secured by Letters Patent of the United States is:

1. A semiconductor device comprising:

a semiconductor body comprising silicon having a (110) plane;

a depression formed by an anisotropic etch applied to a first surface of the semiconductor body, wherein the first surface is substantially parallel to the (110) plane; and a thin film insulation member having a predetermined configuration suspended over the depression, and having substantially opposing ends connected to the first surface of the semiconductor body so that said thin film insulation member is bridged across the depression.

2. A semiconductor device according to claim 1, wherein a depth of the depression is over 200 μm.

3. A semiconductor device according to claim 1, wherein the predetermined configuration of the thin film insulation member is oriented substantially parallel to a <100> direction of the semiconductor body.

4. A semiconductor device according to claim 3, wherein a depth of the depression is over 200 μm.

5. A semiconductor device according to claim 1, wherein the predetermined configuration of the thin film insulation member is oriented substantially parallel to a <111> direction of the semiconductor body.

6. A semiconductor device according to claim 5, wherein a depth of the depression is over 200 μm.

7. A semiconductor device according to claim 1, wherein the predetermined configuration is oriented at an angle to a <100> direction, the angle being under 35.26°.

8. A semiconductor device according to claim 7, wherein a depth of the depression is over 200 μm.

9. A semiconductor device according to claim 1, wherein the predetermined configuration of the thin film insulation member is oriented at an angle to a <111> direction, the angle being under 19.47°.

10. A semiconductor device according to claim 9, wherein a depth of the depression is over 200 μm.

* * * * *